United States Patent [19]

Shionoya et al.

[11] Patent Number: 4,459,287
[45] Date of Patent: Jul. 10, 1984

[54] IMMUNOPOTENTIATOR CONTAINING RECIN

[75] Inventors: Hiroshi Shionoya, Saitama; Haruyoshi Arai, Aichi; Nozomu Koyanagi, Saitama; Hitoshi Takeuchi, Tokyo, all of Japan

[73] Assignee: Eisai Co., Ltd., Tokyo, Japan

[21] Appl. No.: 389,456

[22] Filed: Jun. 17, 1982

Related U.S. Application Data

[63] Continuation of Ser. No. 204,787, Nov. 7, 1980, abandoned.

[30] Foreign Application Priority Data

Nov. 9, 1979 [JP] Japan .................................. 54/144327

[51] Int. Cl.$^3$ ...................... A61K 37/00; A61K 39/00
[52] U.S. Cl. ........................................ 424/88; 424/177
[58] Field of Search ................................. 424/88, 177

[56] References Cited

U.S. PATENT DOCUMENTS 3,060,165  10/1962  Craig et al. .......................... 424/177

FOREIGN PATENT DOCUMENTS 1522600  8/1978  United Kingdom .

OTHER PUBLICATIONS

Olsnes et al., The Journal of Mamunology, vol. 113, No. 3, Sep. 1974, pp. 842–847.
Brochem. & Biophysical Research Communications, vol. 88, No. 3, 1979, Jun. 13, 1979, pp. 818–825.
Microbiology, Harper & Row Publishers, p. 458 (1967).
Proteins, Nucleic Acids, Enzymes; separate print Immuno-Biochemistry, vol. 11, No. 15, p. 1506 (1966).
Scand. J. Immunol., 5, 299 (1976).
J. Biol. Chem., 249, pp. 803–810 (1974).
The Merck Index, 9th Edition (1976), p. 1067.
Nature, vol. 249 (1974), pp. 627–630.
Agric. Biol. Chem. 41 (10), 2041–2046 (1977).

Primary Examiner—Stanley J. Friedman
Attorney, Agent, or Firm—Wenderoth, Lind & Ponack

[57] ABSTRACT

An immunopotentiator comprising ricin as an active ingredient. Ricin is a glucoprotein having a molecular weight of about 65,000 and can be used in the form of an aqueous solution. It is useful for prevention and treatment of bacterial and viral infections and cancer.

1 Claim, No Drawings

IMMUNOPOTENTIATOR CONTAINING RECIN

This application is a continuation of application Ser. No. 204,787, filed Nov. 7, 1980 (now abandoned).

BACKGROUND OF THE INVENTION

This invention relates to an immunopotentiator comprising ricin as an active ingredient.

Ricin used in this invention is a lectin isolated from the seeds of castor beans which is a plant of the Euphorbiaceae and is a kind of glycoprotein having a molecular weight of about 65,000.

Immune protection in vertebrates is known to be provided by two basic immune response systems against infections and tumor cells. One is the cellular immune response system effective mainly against infections by fungi, viruses, intracellular parasitic bacteria, etc. and against tumor cells, and the other is the humoral immune response system effective for defense mainly against infections by viruses and extracellular parasitic bacteria.

A substance which when injected into a living organism together with an antigen, increases the aforesaid immune responses to the antigen is known as an immuno-adjuvant [Davis, B. D. et al., Microbiology, Harper & Row Publishers, page 458, (1967)]. Heretofore, the Freund's complete adjuvant has been used mainly as the immuno-adjuvant. Since, However, the Freund's complete adjuvant is composed of killed Mycobacteria, a surface-active agent and a mineral oil, a complex operation is required for formulating it into a dosage form by mixing it with an antigen in the form of an aqueous solution, a suspension, etc., and moreover, strong necrosis or swelling occurs at the injected site. Accordingly, the Freund's complete adjuvant has been unable to be used in humans.

SUMMARY OF THE INVENTION

It is an object of this invention to provide an immunopotentiator having the ability to increase both cellular and humoral immune responses.

According to this invention, there is provided an immunopotentiator comprising ricin as an active ingredient.

DETAILED DESCRIPTION OF THE INVENTION

Ricin used as the active ingredient of the immunopotentiator of this invention is an immuno-adjuvant having the ability to potentiate both the aforesaid cellular and humoral immune responses. It is characterized by having a strong adjuvant activity in amounts which do not cause necrosis, swelling, etc. at a site of injection. The ricin in accordance with this invention also has the advantage that since it can be used in the form of an aqueous solution, it can be easily formulated into a dosage form by mixing with an antigen.

As to the acute toxicity of ricin used in this invention, experiments of the present inventors showed that $LD_{50}$ of ricin is 12 μg/kg (mouse, i. p.).

When administered to man and animals the ricin of this invention increases immune responses to bacteria, viruses and other microorganisms and tumor cells, and is therefore useful for prevention and treatment of infections by microorganisms such as bacteria and viruses or cancer.

The minimum dosage of ricin which shows an immunopotentiating activity is about 0.2 ng per human or animal irrespective of body weight. The maximum dosage is generally about 1 to about 1.5 μg/kg. These dosages are much lower than the lethal dose mentioned above.

Ricin in accordance with this invention may be administered together with various antigens, and the preferred route of administration is subcutaneous, intramuscular or intraperitoneal. Furthermore, ricin can be administered separately from an antigen, and in this case, intravenous and intrapleural administrations are possible in addition to the aforesaid administration routes. Or it may be administered directly to a tumor region. The administrations of ricin are preferably twice a week to once in two weeks.

In administration, the ricin in accordance with this invention may be formulated into any desired injectable form by known formulating methods. For example, it may be in the form of an injecting ampoule containing 0.1 to 1 ml of a physiological saline or a neutral to weakly acidic buffer containing ricin in a concentration of about 100 μg to 1 mg/ml, or an ricin-containing lyophilized ampoule.

The immunopotentiating activity of ricin is illustrated specifically by the following Examples.

EXAMPLE 1

Immunopotentiative effect of ricin on production of humoral antibody in mice

The effect of ricin on the production of a humoral antibody in mice was examined using bovine serum albumin (BSA) as an antigen.

A solution (0.2 ml) obtained by mixing 0.1 ml of a physiological saline containing 1 μg of BSA antigen with 0.1 ml of a physiological saline containing ricin in various amounts from 0.1 ng to 30 ng was subcutaneously injected into the back of mice (female CDF 1) having a body weight of 20 to 23 g (primary immunization). Two weeks later, the same solution was injected into the mice in the same manner (secondary immunization). Twelve days after the secondary immunization, blood was taken from each of the mice, and the plasma was separated.

The antibody titer of the plasma was measured in accordance with a method of hemagglutination of tanned sheep red blood cells passively sensitized with BSA [PROTEINS, NUCLEIC ACIDS, ENZYMES; separate print "IMMUNOBIOCHEMISTRY", Vol. 11, No. 15, page 1506, (1966)]. The results are shown in Table 1.

TABLE 1

Activity of ricin to increase production of an anti-BSA antibody

| Amount of ricin (ng/mouse) | Number of animals | Number of mice having plasma HA titer estimated by BSA-sensitized sheep red blood cell hemagglutination reaction HA titer* 0 | 20 | 40 | 80 | 160 | 320 |
|---|---|---|---|---|---|---|---|
| 0 | 10 | 10 | | | | | |
| 0.1 | 4 | 3 | | | | | 1 |
| 0.3 | 5 | 3 | | 2 | | | |
| 1 | 4 | 1 | 1 | 1 | 1 | | |
| 3 | 5 | | | 2 | 1 | 2 | |
| 10 | 5 | | | | | 2 | 3 |

TABLE 1-continued

Activity of ricin to increase production of an anti-BSA antibody

| Amount of ricin (ng/mouse) | Number of animals | Number of mice having plasma HA titer estimated by BSA-sensitized sheep red blood cell hemagglutination reaction HA titer* | | | | | |
|---|---|---|---|---|---|---|---|
| | | 0 | 20 | 40 | 80 | 160 | 320 |
| 30 | 5 | | 2 | 1 | 1 | 1 | |

*HA titer = hemagglutination titer

As is apparent from Table 1, immunopotentiative activity of ricin on humoral antibody product was recognized in the range of 1 ng-30 ng per mouse and was in the maximum at 10 ng.

EXAMPLE 2

Immunopotentiative effect of ricin on cellular immune response in mice

A physiological saline (0.2 ml) containing 1 μg of BSA and various amounts of ricin was injected subcutaneously into the back of mice (female CDF 1) having a body weight of 20 to 23 g and being 8-10 weeks old, and two weeks later, the mice were treated with injection in the same way as above (secondary immunization). Twenty-seven days after the secondary immunization, 10 μl of a physiological saline containing 10 μg of BSA was injected subcutaneously into the auricle of each mouse (challenge), in accordance with the method of J. H. Robinsons et al. [Scand. J. Immunol., 5, 299 (1976)]. Twenty-four hours later, the ear swelling was measured. The results are shown in Table 2.

TABLE 2

Cellular Immuno-potentiative Activity of Ricin

| Groups | Number of Animals | Immunization Ricin (ng/mouse) | Immunization BSA (μg/mouse) | Challenge BSA (μg/mouse) | Ear swelling ($10^{-3}$ cm ± S.E.*) | Significance against control (p) |
|---|---|---|---|---|---|---|
| Control | 6 | 0 | 1 | 10 | 5.0 ± 1.2 | — |
| 1 | 4 | 0.3 | 1 | 10 | 8.8 ± 1.9 | <0.05 |
| 2 | 4 | 1 | 1 | 10 | 8.3 ± 1.3 | <0.05 |
| 3 | 5 | 3 | 1 | 10 | 11.0 ± 1.5 | <0.01 |
| 4 | 5 | 10 | 1 | 10 | 16.8 ± 1.6 | <0.01 |
| 5 | 5 | 30 | 1 | 10 | 10.2 ± 1.9 | <0.01 |

*S.E. = standard error

The results of Table 2 reveals that ricin used in an amount ranging from 3 ng to 30 ng enhances the cellular immune response against BSA.

EXAMPLE 3

Potentiative Activity of Ricin on Immunogenicity of Tumor Vaccine

When ricin which has a cytotoxic effect is mixed with tumor cells, the cells lose their tumorigenicity and can thus be used as a tumor vaccine.

Meth-A tumor cells of Balb/c mice origin were used as a source of tumor vaccine to investigate the potentiative activity of ricin on immunogenicity of the tumor vaccine.

Female Balb/c mice, each weighing 20-23 g and being 8-10 weeks old, was injected (immunized) subcutaneously on their right side of the back with 0.1 ml of the Dulbecco's phosphate buffers (pH 7.2) (hereinafter abbreviated as PBS) containing $1 \times 10^4$ Meth-A cells and different amounts of ricin. Two weeks after the immunization, mice were challenged by injecting 0.1 ml of PBS containing $1 \times 10^6$ Meth-A tumor cells subcutaneously on the left side of the back. 28 Days after the challenge, the number of mice that rejected the tumor and the tumor weight of tumor-bearing mice were measured. The results are shown in Table 3.

TABLE 3

| Groups | Number of Animals | Immunization Ricin (ng/mouse) | Immunization Meth-A cells (cells/mouse) | Ratio of rejection | Average tumor weight of tumor bearing mice (g ± S.E.) |
|---|---|---|---|---|---|
| Control | 19 | 0 | 0 | 0/19 | 1.80 ± 0.27 |
| 1 | 10 | 0.2 | $1 \times 10^4$ | 3/10 | 0.83 ± 0.34* |
| 2 | 10 | 0.6 | $1 \times 10^4$ | 5/10** | 1.57 ± 0.31 |
| 3 | 10 | 2.0 | $1 \times 10^4$ | 4/10* | 1.30 ± 0.26 |
| 4 | 10 | 6.0 | $1 \times 10^4$ | 3/10 | 1.41 ± 0.27 |

*p <0.05
**p <0.01

The results of Table 3 reveal that ricin used in an amount ranging from 0.2 to 2 ng potentiates the immunogenicity of the tumor vaccine.

EXAMPLE 4

Preparation of an ricin-containing ampoule

Glacial acetic acid (0.05 ml) was added on ice water bath to 5 ml of an aqueous suspension containing ricin crystals in a concentration of 10 mg/ml to dissolve the ricin crystals. To the resulting solution was added 10 ml of a 0.01 M phosphate buffer (pH 6.0) containing 0.15 M of sodium chloride [to be abbreviated as PBS (pH 6.0)]. Then, 0.4 ml of a 1 M $Na_2HPO_4$ solution was added to adjust the pH of the solution to about 5. The solution was centrifuged at 15000 rpm for 10 minutes. The supernatant solution was filtered by a 0.45 μm filter (Millipore Filter, type HA) to remove microbes. The filtrate was put into a cellophane tube, and dialyzed overnight against 5 liter of PBS (pH 6.0).

The dialyzate was diluted with PBS (pH 6.0) to form a solution containing ricin in a concentration of 500 μg/ml. The concentration of ricin was adjusted according to its $E_{280}^{1\%}$ nm value of 11.8 reported by Olsnes et al. [J. Biol. Chem., 249, 803-810 (1974)]. The ricin solution was put separately in an amount of 0.1 ml into each of 1 ml glass ampoules to prepare injecting ampoules each containing 50 μg of ricin.

What is claimed is:

1. A method for increasing immune response to intracellular parasitic bacteria or extracellular parasitic bacteria in a human or animal subject in need of such treatment which comprises parenterally administering ricin to such human or animal subject to an amount of from at least 0.2 ng per human or animal subject up to about 1.5 μg/kg of body weight of the human or animal subject.

* * * * *